United States Patent [19]
Elokdah et al.

[11] Patent Number: 5,710,164
[45] Date of Patent: Jan. 20, 1998

[54] DIHETEROCYCLIC STYRYL NITRILES

[75] Inventors: Hassan M. Elokdah, Fairless Hills, Pa.; Sie-Yearl Chai, Lawrenceville, N.J.; Theodore S. Sulkowski, Wayne, Pa.

[73] Assignee: American Home Products Corporation, Madison, N.J.

[21] Appl. No.: 470,603

[22] Filed: Jun. 6, 1995

[51] Int. Cl.$^6$ .......................... A61K 31/44; A61K 31/47; C07D 213/04; C07D 215/12
[52] U.S. Cl. .......................... 514/300; 514/314; 514/332; 514/338; 514/339; 514/343; 546/113; 546/176; 546/255; 546/264; 546/276.7; 546/280.4; 546/282.4
[58] Field of Search .......................... 546/113, 176, 546/255, 270, 272, 264; 514/314, 300, 332, 338, 339, 343; 546/276.7, 280.4, 282.4

[56] References Cited

FOREIGN PATENT DOCUMENTS 9116305  10/1991  WIPO .
9218481  10/1992  WIPO .

OTHER PUBLICATIONS

Michalski J. Piechucki C. (1970) Bull. Acad. Pol. Sci., Ser. Sci. Chem. 18(6) 343–5.

*Primary Examiner*—C. Warren Ivy
*Assistant Examiner*—Evelyn Huang
*Attorney, Agent, or Firm*—Rebecca R. Barrett

[57] ABSTRACT

Disclosed herein are compounds of the formula:

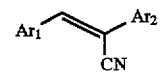

where $Ar_1$ and $Ar_2$ are, independently, pyridinyl, quinolinyl, 1,4-benzodioxanyl, dihydro-1,4-benzodioxanyl, pyrrolyl, azaindolyl or carbazolyl, or a pharmaceutically acceptable salt thereof, which are useful as inhibitors of smooth muscle cell proliferation.

14 Claims, No Drawings

DIHETEROCYCLIC STYRYL NITRILES

BACKGROUND OF INVENTION

Proliferation and directed migration of vascular smooth muscle cells are important vascular occlusive components in such processes as hypertension-induced vascular remodeling, vascular restenosis, and atherosclerosis (Gibbons, G. H.; Dzau, V. J.; NEJM, 1994; 330: 1431). The overall disease process is referred to as hyperproliferative vascular disease based on the etiology of the disease process. Vascular occlusion is preceded by stenosis resulting from intimal smooth muscle cell hyperplasia (Clowes, A. W.; Reidy, M. A.; J. Vasc. Surg., 1991, 13: 885). The underlying cause of intimal smooth muscle cell hyperplasia is vascular smooth muscle cell injury leading to disruption of the endothelium and extracellular matrix (Schwartz, S. M., Human Pathology, 1987; 18: 240; Fingerle, J., Arteriosclerosis, 1990; 10: 1082). Normally, the cells of the arterial wall are under close negative control and in a low basal proliferating state or in a quiescent non-proliferating state. Following vascular injury, the release of growth factors and cytokines result in smooth muscle cell proliferation and migration (Fagin, J. A.; Forrester, J. S., Trends in Cardiovascular Med., 1992; 2; 90.; Shiratani, M.; Yui, Y.; Kawai, C., Endothelium, 1993; 1: 5).

Vascular injury leading to intimal hyperplasia can be induced immunologically or by invasive cardiovascular procedures. Atherosclerosis is a common form of biologically mediated vascular injury progressing to stenosis. Abnormal proliferation of vascular smooth muscle cells is a feature of atherosclerotic plaques responsible for obstructive neointimal lesions at the site of intimal damage (Ross, R., Nature, 1993: 362; 801; Cascells, W., Circulation, 1992; 86: 723). Mechanical injury leading to intimal hyperplasia can occur following angioplasty procedures, organ transplant surgery and other vascular invasive procedures that disrupt vascular integrity (Clowes, A. W.; Reidy, M. A., J. Vasc. Surg., 1991; 13: 885; Isik, F. F.; McDonald, T. O.; Ferguson, M.; Yanaka, E., Am. J. Pathol., 1992; 141: 1139).

Percutaneous transluminal coronary angioplasty has achieved wide acceptance for the treatment of coronary artery stenosis. In this procedure the endothelium is damaged and exposed to a variety of chemoattractants and mitogens which are either blood-borne or are released at the site of injury. Among these agents, platelet-derived growth factor (PDGF) is thought to play a significant role in the process of smooth muscle cell proliferation and chemotaxis (Reidy, M. A.; Fingerle, J.; Lindner, V.; Circulation, 1993: 86 (suppl III): III-43.; Ferns, G. A. A.; Raines, E. W.; Sprugel, K. H.; Montani, A. S.; Reidy, M. A.; Ross, R.; Science, 1991; 253: 1129.; Jawien, A., et al., J. Clin. Invest., 1992; 89: 507; Nabel, E. G., et al., J. Clin. Invest., 1993; 91: 1822). Within 3 to 6 months after angioplasty, a significant reduction in blood flow occurs in approximately 30-40% of patients as a result of restenosis caused by response to vascular injury during this procedure. These patients then require a second interventional procedure (Pepine, C., Circulation, 1990; 81: 1753.; Hardoff, R. J., J. Am. Coll. Cardiol., 1990; 15: 1486). Accordingly, agents that limit the restenosis process would be of significant benefit. Agents that inhibit vascular smooth muscle cell proliferation, particularly PDGF-stimulated proliferation, would be useful in the treatment of vascular hyperproliferative disorders (Molloy, C. J., Drug Dev. Res., 1993; 29: 148.; Newby, A. C.; George, S. J., Cardiovasc. Res., 1993; 27: 1173).

WO 9218481 discloses 3-heteroaryl-2-phenyl-2-propenenitriles as EGF receptor tyrosine kinase inhibitors useful for inhibition of cell proliferation. WO 9116305 discloses some mono and some 2,3-diheterocyclic propene nitriles as cellular antiproliferative agents.

DESCRIPTION OF THE INVENTION

This invention relates to the use of diheterocyclic styryl nitrile derivatives as smooth muscle cell proliferation inhibitors and as therapeutic compositions for treating diseases and conditions which are characterized by excessive smooth muscle cell proliferation such as restenosis.

In accordance with this invention there is provided a group of of diheterocyclic styryl nitriles of formula I:

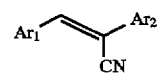

where $Ar_1$ and $Ar_2$ are, independently, pyridinyl, quinolinyl, 1,4-benzodioxanyl, dihydro-1,4-benzodioxanyl, pyrrolyl, azaindolyl or carbazolyl, or a pharmaceutically acceptable salt thereof.

The diheterocyclic styryl nitriles were prepared by the condensation of an appropriate heterocyclic aldehyde ($Ar_1$) with an appropriate heterocyclic acetonitrile ($Ar_2$). The condensation is carried out in ethanol using piperidine or sodium methoxide as a base.

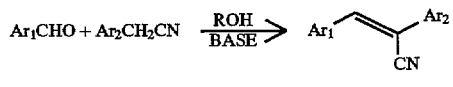

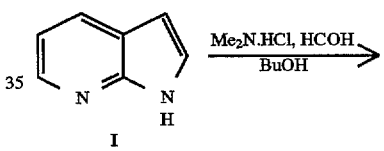

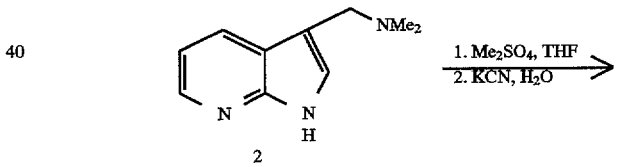

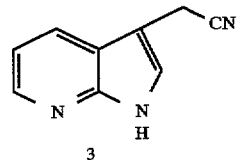

When $Ar_2$ is 7-azaindole, 7-azaindole acetonitrile (3) is prepared by reacting 7-azaindole with dimethylamine and formaldehyde in refluxing butanol to obtain 7-(3-dimethylaminomethyl) azaindole (2). Quaternization of (2) with dimethylsulfate in tetrahydrofuran, followed by reaction with potassium cyanide in water affords the acetonitrile (3).

The pharmaceutically acceptable salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids.

This invention includes pharmaceutical compositions comprised of the diheterocyclic styryl nitriles of the invention either alone or in combination with excipients (i.e. pharmaceutically acceptable materials with no pharmacological effect). Such compositions are useful in treating diseases which are characterized by excessive smooth muscle cell proliferation most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of this invention are thus useful for treating these diseases and states.

The compounds of this invention may be administered systemically, for example by intravenous injection, typically ranging from 0.1 to 10 mg/kg/h over 5–30 days, by subcutaneous injection at lower dose or by oral administration at higher dose than intravenous injection. Localized delivery of the compounds of this invention may also be achieved by transmembrane, transdermal or other topical administrative routes using appropriate continuous release devices such as a supporting matrix, where applicable. The compositions of the invention may be formulated with conventional excipients, such as a filler, a disintegrating agent, a binder, a lubricant, a flavoring agent and the like. These are formulated in a conventional manner.

The compounds may be administered neat or with a solid or liquid pharmaceutical carrier to a patient in need of such treatment. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the freely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously.

Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from a disease involving smooth muscle cell proliferation must be subjectively determined by the attending physician. The variables involved include the specific disease state and the size, age and response pattern of the patient.

The ability of the compounds of the present invention to inhibit smooth muscle cell proliferation was established using isolated porcine aortic smooth muscle cells in a modification of the procedure of Castellot et al. J. Biol. Chem 257(19) 11256 (1982), as follows:

Fresh porcine aortas, scrupulously cleansed of fatty tissue, are rinsed in sterile phosphate-buffered saline with 2% antibiotic-antimycotic (100×) liquid (10,000 units of penicillin (base), 10,000 µg of streptomycin (base), and 25 µg of amphotericin B/mL utilizing penicillin G (sodium salt), streptomycin sulfate, and amphotericin B as Fungizone® in 0.85% saline, available from Gibco Laboratories, Grand Island Biological Co., Grand Island, N.Y.). The tissue is then digested in 10–15 mL of an enzyme solution containing collagenase type I, 165 U/mL; elastase type III, 15 U/mL; BSA, 2 mg/mL; and soybean trypsin inhibitor, 0.375 mg/mL, followed by incubation at 37° C. under 5% $CO_2$ atmosphere for 10 to 15 minutes. After this treatment, the outer surface adventitia is removed by peeling with a forceps. The aorta is then longitudinally cut and laid open and the endothelial layer is removed by scraping.

The medial layer of cells is rinsed in the enzyme solution, and placed in a new 100 mm dish with 10 mL of enzyme solution. The medial layer of cells is minced using a fine pair of scissors and digested for 2–3 hours at 37° C. in 30 mL of fresh enzyme solution. After digestion, the medial tissue is homogenized using a sterile Pasteur pipette with a fire polished tip or an Eppendorf pipetter with a 200–1000 µL sterile pipette tip. The suspension is then centrifuged for 10 minutes at 8000 rpm and the pellet is suspended in 4–6 mL of fresh enzyme solution and plated onto 4–6 100 mm flasks with vented caps. The cells are then allowed to grow to confluence and split using 0.25% trypsin. The cells are evaluated for purity and overall quality using antibody to SMC actin.

The cells are assayed in early passage (generally passage 3–7) at sub-confluent conditions. Cultures are grown in 16 mm (24 well) multi-well culture dishes in media 199 supplemented with 10% fetal bovine serum and 2% antibiotic/ antimycotic. At subconfluence, the cells are placed in a defined serum free, lymphocyte medium (AIM-V; Gibco) for 24–48 hours prior to initiating the experimental protocol.

The standard test procedure is initiated by addition of the test compound, $^3$H thymidine and serum or a specific growth factor to the serum deprived synchronized cells. Growth factor and serum stimulations are optimized for each cell type. The test compounds are added to each well at 50 fold dilution (20 µL/well) and the plates are incubated for 24–36 hours at 37° C. in 5% $CO_2$ atmosphere. Test compounds are dissolved in 50% ethanol and assayed at 1, 10, and 100 µM. As a control, RG 50872 (Bilder, G. A.; et al., Am. J. Cell Physiol., 1991; 260: C721) is routinely assayed under the conditions of each cell preparation at a concentration of 5 µM.

At the completion of the experiment, the plates are placed on ice, washed three times with ice cold PBS and incubated in ice cold 10% trichloroacetic acid (TCA) for 30 minutes to remove acid soluble proteins. Each solution is transferred to a scintillation vial containing 0.4N HCl (500 µL/vial to neutralize NaOH) and each well is rinsed two times with water (500 µL) for a total volume of 2 mL/vial.

Data is quantitated by subjecting the vials to a scintillation counter, in triplicate, for both control and experimental samples. Control (100%) data is obtained from maximally stimulated cells, as the result of growth factor or serum stimulation. Experimental data is obtained from cells maximally stimulated with growth factor or serum and treated with a test compound. (The platelet-derived growth factor used in the assay was human recombinant PDGF-AB purchased from Upstate Biotechnology Inc., Lake Placid, N.Y.). Data is expressed as a percent of control from which $IC_{50}s$ are determined.

To distinguish cytotoxicity from the ability of a compound to prevent proliferation, the test compounds were examined using a commercial modification of the MTT assay. Briefly, cells were grown in 24 well plates to 70–80% confluency. The cells were serum deprived for 24–48 hours prior to initiation of the experimental protocol. To insure that the MTT assay monitored toxicity rather than proliferation, the cells were incubated with 50 mM test compound in fresh medium without serum for 24 hours at 37° C. in a humidified $CO_2$ incubator. Upon completion of the compound treatment, MTT indicator dye was added for 4 hours at 37° C. Cells were then solubilized and aliquots from each well were transferred to a 96-well plate for analysis. Absorbance at 570 nm wavelength with a reference wavelength of 630 nm was recorded using an ELISA plate reader. Results are reported as percent viable using no drug (100% viable) and pre-solubilization (0% viable) standards.

The compounds of the present invention are effective inhibitors of smooth muscle cell proliferation as shown by the data presented in Table I.

TABLE I

| Compound of Example Number | Porcine Smooth Muscle Cell Antiproliferation $IC_{50}$ or % Inhibition at x Concentration | | Cytotoxicity % Viable |
|---|---|---|---|
| | Serum | PDGF | Cells |
| 1 | 1.159 µM | 0.346 µM | 100 |
| 2 | 81 µM | — | — |
| 3 | 3.8–11.5 µM | 10.5 µM | 86 |
| 4 | 48.3 µM | — | 92 |
| 5 | 96.6 µM | — | — |
| 6 | 1.18 µM | 0.9 µM | 100 |
| 7 | 1.23 µM | 14.8 µM | 100 |
| 8 | 0.355 µM | 0.336 µM | 100 |
| 9 | 92 µM | — | 84 |

The following examples are presented by way of illustration rather than limitation for the production of representative compounds of the invention.

EXAMPLE 1

Z-2-(Pyridin-3yl)-3-(pyridin-4-yl)-acrylonitrile

3-Pyridylacetonitrile (1.18 g; 0.01 mol) and 4-pyridyl carboxyaldehyde (1.07 g; 0.01 mol) were dissolved in ethanol (75 mL). Sodium methoxide (2.16 g of 25% methanol solution, 0.01 mol) was then added. The mixture was allowed to stand at ambient temperature for a period of 1 hour. The crystalline solid that formed was collected by filtration, washed with fresh ethanol and dried to give the title compound (1.0 g, 48% yield) as an off-white solid, m.p. 150°–152° C. Anal. Calcd. for $C_{13}H_9N_3$: C, 75.35; H, 4.38; N, 20.28. Found: C, 75.01; H, 4.58; N, 20.19. Mass spectrum (EI; M$^+$) m/z 207. $^1$H-NMR (DMSO-$d_6$; 400 MHz) δ 9.0 (s, 1H), 8.78 (d, 2H), 8.68 (d, 1H), 8.21 (s, 1H), 8.17 (m, 1H), 7.8 (d, 2H), and 7.58 ppm (m, 1H).

EXAMPLE 2

2-Pyridin-3-yl -3-quinolin-4-yl-acrylonitrile

Quinolin-4-carboxaldehyde (4.71 g; 0.03 mol) and 3-pyridylacetonitrile (3.54 g; 0.03 mol) were dissolved in ethanol (100 mL). Sodium methoxide (2 mL of 25% methanol solution) was added. The reaction mixture was heated at reflux for a period of 2.5 hours. The mixture was cooled to ambient temperature. After 18 hours, the precipitated solid was collected, suspended in ethanol and saturated with hydrogen chloride gas. The mixture was cooled and the solid was collected by filtration. The solid was crystallized from methanol to give the title compound (5.8 g; 57% yield) as a dihydrochloride, three quarter hydrate, yellow solid, m.p. 250° C. (dec.). Anal. Calcd for $C_{17}H_{11}N_3 \cdot HCl \cdot \frac{3}{4} H_2O$; C, 59.40; H, 4.25; N, 12.23. Found: C, 59.75; H, 4.10; N, 11.93. Mass spectrum (EI; M$^+$) m/z 257. $^1$H-NMR (DMSO-$d_6$; 400 MHz) δ 9.40 (s, 1H), 9.38 (d, 1H), 9.15 (s, 1H), 8.93 (d, 1H), 8.74 (d, 1H), 8.56 (d, 1H), 8.46 (d, 1H), 8.32 (d, 1H), 8.13 (t, 1H), 8.00 (q, 1H), 7.95 (t, 1H), and 7.70 ppm (br s, 4H).

EXAMPLE 3

3-(2,3-Dihydro-benzo[1,4]dioxin-6-yl)-2-pyridin-3-yl-acrylonitrile

To the solution of 2,3-dihydro-benzo[1,4]dioxin-6-carboxaldehyde (4.92 g; 0.03 mol) and 3-pyridylacetonitrile (3.54 g; 0.03 mol) in ethanol (100 mL) was added sodium methoxide (6.48 g, of 25% methanol solution, 0.03 mol). The mixture was allowed to stand at ambient temperature for 18 hours. The mixture was concentrated to half volume. The solid was collected by filtration and dried to give 7.0 g (88.4% yield) of the title compound as an off-white solid, m.p. 158°–159° C. Anal. Calcd. for $C_{16}H_{12}N_2O_2$: C, 72.72; H, 4.58; N, 10.60. Found: C, 72.53; H, 4.48; N, 10.97. Mass spectrum (DEI; M$^+$) m/z 264. $^1$H-NMR (DMSO-$d_6$; 400 MHz) δ 8.91 (d, 1H), 8.59 (d, 1H), 8.08 (d, 1H), 8.00 (s, 1H), 7.57 (d, 1H), 7.47–7.53 (m, 2H), 7.02 (d, 2H), and 4.31 ppm (m, 4H).

EXAMPLE 4

2-Pyridin-3-yl-3-pyridin-2-yl-acrylonitrile

The title compound was prepared by the procedure described in Example 1 using 2.14 g (0.02 mol) of 2-pyridylcarboxyaldehyde and equivalent amounts of all other reactants. After standing at ambient temperature for a period of 18 hours, the crystalline solid was collected by filtration and dried to afford the title compound (3.0 g; 72.5% yield) as a yellow solid, m.p. 115°–117° C. Anal. Calcd. for $C_{13}H_9N_3$: C, 75.34; H, 4.38; N, 20.28. Found: C, 75.31; H, 4.32; N, 20.28. Mass spectrum (EI; M$^+$) m/z 207. $^1$H-NMR (DMSO-$d_6$; 400 MHz) δ 9.01 (d, 1H), 8.76 (d, 1H), 8.66 (dd, 1H), 8.19 (m, 1H), 8.15 (s, 1H), 7.97 (td, 1H), 7.76 (d, 1H), 7.56 (q, 1H), and 7.49 ppm (m, 1H).

EXAMPLE 5

2,3-Di-pyridin-3-yl-acrylonitrile

The title compound was prepared by the procedure described in Example 1 using 2.14 g (0.02 mol) of 3-pyridylcarboxyaldehyde and equivalent amounts of all other reactants. After standing at ambient temperature for 4 hours, the crystalline solid was collected by filtration, washed with ethanol and dried to give 1.6 g (37% yield) of the title compound as an off-white solid, m.p. 136°–137° C. Anal. Calcd. for $C_{13}H_9N_3$: C, 75.34; H, 4.38; N, 20.28. Found: C, 75.31; H, 4.30; N, 20.49. Mass spectrum (EI; $M^+$) m/z 207. $^1$H-NMR (DMSO-$d_6$; 400 MHz) δ 8.99 (dd, 2H), 8.67 (qd, 2H), 8.38 (m, 1H), 8.23 (s, 1H), 8.16 (m, 1H), and 7.58 ppm (m, 2H).

EXAMPLE 6

2-(Pyridin-3-yl)-3-(1H-pyrrolo[2,3-b]pyridin-3-yl)-acrylonitrile

4H-Pyrrolo[2,3-b]pyridin-3-yl carboxyaldehyde (1.46 g; 0.01 mol), 3-pyridylacetonitrile (1.18 g; 0.01 mol) and sodium methoxide (2.16 g of 25% methanol solution, 0.01 mol) were heated to reflux in ethanol (50 mL) for 4 hours. The solvent was evaporated to the precipitation point. The mixture was then filtered and the solid was collected and dried. The solid was suspended in water and stirred for 1 hour. The solid was then collected by filtration and dried under vacuum for 18 hours to give 1.4 g (57% yield) of the title compound as a yellow solid, m.p. 295°–297° C. (dec.). Anal. Calcd. for $C_{15}H_{10}N_4$: C, 73.16; H, 4.09; N, 22.75. Found: C, 72.99; H, 3.86; N, 22.68. Mass spectrum (+DCI, [M+H]$^+$ m/z 247. $^1$H-NMR (DMSO-$d_6$, 400 MHz) δ 12.63 (br s, 1H), 8.99 (d, 1H), 8.56 (m, 2H), 8.45 (s, 1H), 8.39 (s, 1H), 8.36 (dd, 1H), 8.18 (m, 1H), 7.52 (q, 1H), and 7.27 ppm (q, 1H).

EXAMPLE 7

Step 1

Dimethyl-(1H-pyrrolo[2,3-b]pyridin-3-ylmethyl)-amine

A mixture of 1H-pyrrolo[2,3-b]pyridine (59 g; 0.5 mol), dimethylamine hydrochloride (44.83 g; 0.55 mol) and paraformaldehyde (16.5 g; 0.55 mol) in n-butanol (700 mL) was heated at reflux for 20 minutes. The mixture was cooled to ambient temperature. The precipitated solid was collected by filtration and dried. The solid was then dissolved in water (800 mL), a few drops of HCl was added for complete solution. The aqueous solution was washed with diethyl ether. Solid potassium carbonate was then added to the aqueous phase until basic. The precipitated solid was collected, washed with water and dried to give 43.5 g (50% yield) of the title compound as an off-white solid, m.p. 161°–162° C. Anal. Calcd. for $C_{10}H_{13}N_3$: C, 68.54; H, 7.48; N, 23.95. Found: C, 68.28; H, 7.75; N, 23.99. Mass spectrum (DEI; $M^+$) m/z 175. $^1$H-NMR (DMSO-$d_6$; 400 MHz) δ 12.45 (br s, 1H), 8.14 (dd, 1H), 7.97 (dd, 1H), 7.32 (s, 1H), 7.01 (q, 1H), 3.51 (s, 2H), and 2.12 ppm (s, 6H).

Step 2

1H-Pyrrolo[2,3-b]pyridin-3-yl-acetonitrile

A solution of dimethylsulfate (32.7 g; 0.25 mol) in THF (50 mL) was added dropwise while stirring to the solution of dimethyl-(1H-pyrrolo[2,3-b]-pyridinyl-methyl)-amine (42 g; 0.24 mol) in THF (800 mL). After the addition was complete, the mixture was heated at 80° C. for 10 minutes then cooled to ambient temperature. The solvent was decanted and the residual gum was triturated with acetone/methanol (1:1 mixture) while warming. The solid formed was collected by filtration. The solid was then dissolved in water (500 mL). Potassium cyanide (22 g; 0.32 mol) was added. The mixture was stirred at ambient temperature for 15 minutes, heated to reflux for 30 minutes, then cooled to ambient temperature. After 2 hours, the solid was collected by filtration and washed with water then dried to give 21 g (56% yield) of the title compound as an off-white solid, m.p. 141°–142° C. which was used for the reaction described in step 3.

Step 3

(Z)-3-(2,3-Dihydro-benzo[1,4]dioxin-6-yl)-2-(1H-pyrrolo-[2,3-b]pyridin-3-yl)-acrylonitrile A mixture of 1-H-pyrrolo[2,3-b]pyridinyl-acetonitrile (3.14 g; 0.02 mol), 2,3-dihydro-benzo[1,4]dioxin-6-carboxyaldehyde (3.3 g; 0.02 mol) and sodium methoxide (4.32 g, of 25% methanol solution, 0.02 mol) was heated to reflux in ethanol (50 mL) for a period of 1 hour. The mixture was concentrated to half its volume. The formed solid was collected by filtration. The solid was washed with water and dried. It was then suspended in ethyl acetate/methanol (1:1, 100 mL) and the resulting mixture was saturated with hydrogen chloride. The mixture was cooled to ambient temperature while stirring. The solid was collected by filtration and dried to give 2.3 g (40% yield) of the title compound as a mono-hydrochloride, yellow solid, m.p. 280°–283° C. (dec.). Anal. Calcd. for $C_{18}H_{13}N_3O_2 \cdot HCl$: C, 63.63; H, 4.16; N, 12.37. Found: C, 68.83; H, 3.95; N, 12.31. Mass spectrum (+DCI, [M+H]$^+$) m/z 304. $^1$H-NMR (DMSO-$d_6$, 400 MHz) δ 12.55 (br s, 1H), 9.35 (br s, 1H), 8.6 (dd, 1H), 8.39 (dd, 1H), 7.91 (s, 1H), 7.71 (s, 1H), 7.53 (d, 1H), 7.45 (dd, 1H), 7.31 (q, 1H), 7.0 (d, 1H), and 4.30 ppm (m, 4H).

EXAMPLE 8

(Z)-3-(9-Ethyl-9H-carbazol-3-yl)-2-(pyridin-3-yl) acrylonitrile

9-Ethyl-9H-carbazol-3-yl-carboxaldehyde (4.46 g; 0.02 mol) and 3-pyridylacetonitrile (2.36 g; 0.02 mol) were dissolved in ethanol (25 mL). Sodium methoxide (1 mL of 25% methanol solution) was added. The mixture was then left standing at ambient temperature for 24 hours. The formed precipitate was collected by filtration and dried to give 2.4 g (37% yield) of the title compound as a yellow solid, m.p. 131°–133° C. Anal. Calcd. for $C_{22}H_{17}N_3$: C, 81.71; H, 5.30; N, 12.99. Found: C, 81.38; H. 5.49; N, 12.84. Mass spectrum (EI; $M^+$) m/z 323. $^1$H-NMR (DMSO-$d_6$; 400 MHz) δ 8.98 (d, 1H), 8.75 (d, 1H), 8.60 (dd, 1H), 8.28 (s, 1H)1, 8.18 (dd, 1H), 8.12–8.16 (m, 2H), 7.8 (d, 1H), 7.68 (d, 1H), 7.51–7.56 (m, 2H), 7.29 (t, 1H), 4.49 (q, 2H), and 1.34 ppm (t, 3H).

EXAMPLE 9

2-(Pyridin-3-yl)-3-(1H-pyrrol-2-yl)-acrylonitrile

A mixture of pyrrole-2-carboxaldehyde (2.85 g; 30 mmol), 3-pyridylacetonitrile (3.54 g; 30 mmol), and piperidine (2 mL) in methanol (50 mL) was refluxed for 18 hours.

The dark precipitate formed was separated by filtration. Dark solid was treated with charcoal in hot methanol to obtain 2.8 g (48%) of the title compound as a yellow solid, m.p. 139°–142° C. Anal. Calcd. for $C_{12}H_9N_3$: C, 73.83; H, 4.65; N, 21.52. Found: C, 73.71; H, 4.57; N, 21.76. Mass spectrum: (EI; M$^+$) m/z 195. $^1$H-NMR (DMSO-d$_6$; 200 MHz) δ 11.5 (s, 1H), 8.8 (d, 1H), 8.5 (d, 1H), 7.92–7.96 (m, 1H), 7.8 (s, 1H), 7.43–7.52 (m, 1H), 7.2 (d, 2H), 6.38–6.4 ppm (q, 1H).

What is claimed is:

1. A compound of the formula:

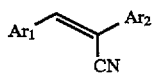   I where $Ar_1$ and $Ar_2$ are, independently, pyridinyl, quinolinyl, 1,4-benzodioxanyl, 2,3-dihydro-1,4-benzodioxanyl, pyrrolyl, azaindolyl, carbazolyl or 9-ethylcarbazolyl or a pharmaceutically acceptable salt thereof, with the proviso that $Ar_1$ and $Ar_2$ are not both 2-pyridinyl and at least one of $Ar_1$ and $Ar_2$ is a 3-pyridinyl.

2. A compound selected from the group consisting of

Z-2-(pyridin-3yl)-3-(pyridin-4-yl)-acrylonitrile;

2-pyridin-3-yl-3-quinolin-4-yl-acrylonitrile;

3-(2,3-dihydro-benzo[1,4]dioxin-6-yl)-2-pyridin-3-yl-acrylonitrile;

2-pyridin-3-yl-3-pyridin-2-yl-acrylonitrile;

2,3-di-pyridin-3-yl-acrylonitrile;

2-(pyridin-3-yl)-3-(1H-pyrrolo[2,3-b]pyridin-3-yl)-acrylonitrile; (Z)-3-(2,3-dihydro-benzo[1,4]dioxin-6-yl)-2-(1H-pyrrolo[2,3-b]pyridin-3-yl)-acrylonitrile;

(Z)-3-(9-ethyl-9H-carbazol-3-yl)-2-(pyridin-3-yl) acrylonitrile; and 2-(pyridin-3-yl)-3-(1H-pyrrol-2-yl)-acrylonitrile or a pharmaceutically acceptable salt thereof.

3. The compound of claim 2 which is Z-2-(pyridin-3-yl)-3-(pyridin-4-yl)-acrylonitrile or a pharmaceutically acceptable salt thereof.

4. The compound of claim 2 which is 2-pyridin-3-yl-3-quinolin-4-yl-acrylonitrile or a pharmaceutically acceptable salt thereof.

5. The compound of claim 2 which is 3-(2,3-dihydro-benzo[1,4]dioxin-6-yl)-2-pyridin-3-yl-acrylonitrile or a pharmaceutically acceptable salt thereof.

6. The compound of claim 2 which is 2-pyridin-3-yl-3-pyridin-2-yl-acrylonitrile or a pharmaceutically acceptable salt thereof.

7. The compound of claim 2 which is 2,3-di-pyridin-3-yl-acrylonitrile or a pharmaceutically acceptable salt thereof.

8. The compound of claim 2 which is 2-(pyridin-3-yl)-3-(1H-pyrrolo[2,3-b]-pyridin-3-yl)-acrylonitrile or a pharmaceutically acceptable salt thereof.

9. The compound of claim 2 which is (Z)-3-(2,3-dihydro-benzo[1,4]dioxin-6-yl)-2-(1H-pyrrolo[2,3-b]pyridin-3-yl)-acrylonitrile or a pharmaceutically acceptable salt thereof.

10. The compound of claim 2 which is (Z)-3-(9-ethyl-9H-carbazol-3-yl)-2-(pyridin-3-yl) acrylonitrile or a pharmaceutically acceptable salt thereof.

11. The compound of claim 2 which is 2-(pyridin-3-yl)-3-(1H-pyrrol-2-yl)-acrylonitrile or a pharmaceutically acceptable salt thereof.

12. A pharmaceutical composition comprising a compound of formula:

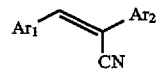   I where $Ar_1$ and $Ar_2$ are, independently, pyridinyl, quinolinyl, 1,4-benzodioxanyl, 2,3-dihydro-1,4-benzodioxanyl, pyrrolyl, azaindolyl, carbazolyl or 9-ethylcarbazolyl or a pharmaceutically acceptable salt thereof, with the proviso that at least one of $Ar_1$ $Ar_2$ is a 3-pyridinyl.

13. A method for preventing smooth muscle cell proliferation in a mammal which comprises administering to that mammal, orally or parentally, a compound of formula:

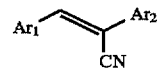   I where $Ar_1$ and $Ar_2$ are, independently, pyridinyl, quinolinyl, 1,4-benzodioxanyl, 2,3-dihydro-1,4-benzodioxanyl, pyrrolyl, azaindolyl, carbazolyl or 9-ethylcarbazolyl or a pharmaceutically acceptable salt thereof, with the proviso that at least one of $Ar_1$ and $Ar_2$ is a 3-pyridinyl.

14. A method according to claim 13 wherein said smooth muscle cell proliferation manifests itself as restenosis following angioplasty.

* * * * *